United States Patent
Itai

(10) Patent No.: US 10,806,392 B2
(45) Date of Patent: Oct. 20, 2020

(54) CARTILAGE QUANTIFICATION DEVICE, CARTILAGE QUANTIFICATION METHOD, AND CARTILAGE QUANTIFICATION PROGRAM

(71) Applicant: FUJIFILM Corporation, Tokyo (JP)

(72) Inventor: Yoshinori Itai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 71 days.

(21) Appl. No.: 15/638,999

(22) Filed: Jun. 30, 2017

(65) Prior Publication Data

US 2018/0070874 A1    Mar. 15, 2018

(30) Foreign Application Priority Data

Sep. 14, 2016    (JP) .................. 2016-179259

(51) Int. Cl.
| | |
|---|---|
| *G06K 9/00* | (2006.01) |
| *A61B 5/00* | (2006.01) |
| *A61B 5/107* | (2006.01) |
| *G06T 7/00* | (2017.01) |
| *G06T 7/40* | (2017.01) |

(52) U.S. Cl.
CPC .......... *A61B 5/4514* (2013.01); *A61B 5/0013* (2013.01); *A61B 5/0035* (2013.01); *A61B 5/107* (2013.01); *A61B 5/72* (2013.01); *G06T 7/0012* (2013.01); *G06T 7/40* (2013.01); *G06T 7/97* (2017.01); *G06T 2207/10081* (2013.01); *G06T 2207/10088* (2013.01); *G06T 2207/30008* (2013.01)

(58) Field of Classification Search
CPC ... A61B 5/0013; A61B 5/0035; A61B 5/4514; A61B 5/72; G06T 2207/30008; G06T 7/0012; G06T 7/40; G06T 7/97; G06T 2207/30004
See application file for complete search history.

(56) References Cited

U.S. PATENT DOCUMENTS

| | | | | |
|---|---|---|---|---|
| 8,696,603 | B2 * | 4/2014 | Takahashi | G06T 7/60 600/595 |
| 8,907,949 | B2 * | 12/2014 | Sakuragi | G06T 7/66 345/424 |

(Continued)

FOREIGN PATENT DOCUMENTS

| | | |
|---|---|---|
| JP | 2002-532126 A | 10/2002 |
| JP | 2009-512524 A | 3/2009 |

(Continued)

OTHER PUBLICATIONS

Japanese Office Action, dated May 21, 2019, for Japanese Application No. 2016-179259, with an English translation.

*Primary Examiner* — Avinash Yentrapati
(74) *Attorney, Agent, or Firm* — Birch, Stewart, Kolasch & Birch, LLP

(57) ABSTRACT

A region extraction unit extracts a bone region and a cartilage region from a three-dimensional image. A projection direction determination unit determines a projection direction of the cartilage region and a projection image generation unit projects the bone region and the cartilage region in the determined projection direction and generates a projection image. A quantification unit calculates a quantitative value of the cartilage region on the projection image.

18 Claims, 11 Drawing Sheets

(56) References Cited

U.S. PATENT DOCUMENTS

| | | | | |
|---|---|---|---|---|
| 9,001,969 B2* | 4/2015 | Murakoshi | A61B 6/4233 | 378/87 |
| 9,024,941 B2* | 5/2015 | Itai | G06T 19/003 | 345/419 |
| 10,062,184 B2* | 8/2018 | Sakuragi | A61B 6/467 | |
| 2002/0087274 A1* | 7/2002 | Alexander | A61B 5/7275 | 702/19 |
| 2004/0136583 A1* | 7/2004 | Harada | G06T 7/0012 | 382/131 |
| 2007/0015995 A1* | 1/2007 | Lang | A61B 5/1038 | 600/407 |
| 2008/0137934 A1* | 6/2008 | Sakaguchi | A61B 6/503 | 382/132 |
| 2008/0312663 A1* | 12/2008 | Haimerl | G06T 7/0012 | 606/130 |
| 2009/0190815 A1* | 7/2009 | Dam | G06T 7/0012 | 382/131 |
| 2010/0145231 A1* | 6/2010 | Takahashi | G06T 7/0012 | 600/587 |
| 2010/0150418 A1* | 6/2010 | Moriya | G06T 19/00 | 382/128 |
| 2010/0198513 A1* | 8/2010 | Zeng | G01S 17/931 | 701/300 |
| 2012/0136208 A1* | 5/2012 | Itai | G06T 19/003 | 600/109 |
| 2012/0172700 A1* | 7/2012 | Krishnan | A61B 6/5217 | 600/407 |
| 2013/0094732 A1* | 4/2013 | Chabanas | A61B 34/10 | 382/128 |
| 2015/0178989 A1* | 6/2015 | Itai | A61B 5/055 | 382/131 |
| 2015/0317790 A1* | 11/2015 | Choi | G06T 7/0012 | 382/128 |
| 2016/0022173 A1* | 1/2016 | Schubert | A61B 5/1072 | 600/587 |
| 2016/0157726 A1* | 6/2016 | Itai | A61B 5/0084 | 600/476 |
| 2016/0270856 A1* | 9/2016 | Park | G06T 5/50 | |
| 2017/0258526 A1* | 9/2017 | Lang | A61B 17/1703 | |
| 2017/0323443 A1* | 11/2017 | Dhruwdas | G06T 7/0012 | |
| 2018/0070874 A1* | 3/2018 | Itai | A61B 5/72 | |

FOREIGN PATENT DOCUMENTS

| | | |
|---|---|---|
| JP | 2010-305 A | 1/2010 |
| JP | 2013-48788 A | 3/2013 |
| WO | WO 00/35346 A2 | 6/2000 |

\* cited by examiner

FIG. 11
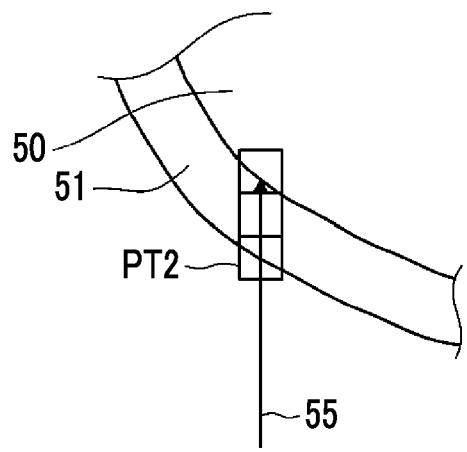
FIG. 12
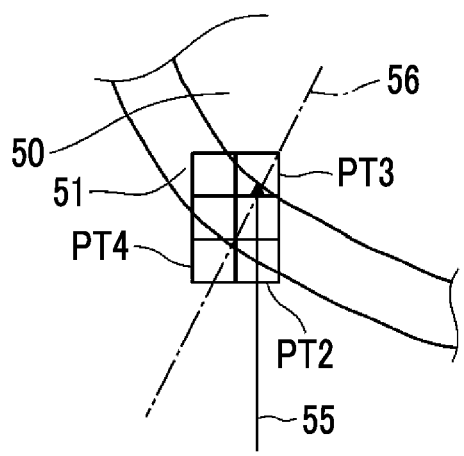
FIG. 13
|  | FRONT RIGHT (A1) | FRONT LEFT (A2) | REAR RIGHT (A3) | REAR LEFT (A4) |
|---|---|---|---|---|
| AREA RATIO | 1.00 | 1.00 | 1.00 | 0.66 |
| DEFICIENCY AREA | 0.00 | 0.00 | 0.00 | 1.02 |
| CARTILAGE THICKNESS | 2.16 | 2.68 | 2.23 | 1.06 |

CARTILAGE QUANTIFICATION DEVICE, CARTILAGE QUANTIFICATION METHOD, AND CARTILAGE QUANTIFICATION PROGRAM

CROSS REFERENCE TO RELATED APPLICATIONS

The present application claims priority under 35 U.S.C. § 119 to Japanese Patent Application No. 2016-179259 filed on Sep. 14, 2016. The above application is hereby expressly incorporated by reference, in its entirety, into the present application.

BACKGROUND

Field of the Invention

The present invention relates to a device, a method, and a program for quantifying cartilage in a joint using a three-dimensional image.

Description of the Related Art

In recent years, a high-quality, high-resolution, three-dimensional image has been used for image diagnosis due to advances in medical devices such as a computed tomography (CT) device and a magnetic resonance imaging (Mill) device. Here, the three-dimensional image is constituted of a large number of two-dimensional images and the amount of information is large. Therefore, in some cases, it takes time for a doctor to find and diagnose a desired observation site. The visibility of an entire organ of interest or a lesion is increased by performing maximum intensity projection (MIP) display through recognizing an organ of interest and extracting the organ of interest from a three-dimensional image including the organ of interest using methods, for example, a MIP method and a minimum intensity projection (MinIP) method, or by performing volume rendering (VR) display of a three-dimensional image, to improve the efficiency of diagnosis.

Meanwhile, osteoarthrosis is a disease developed in many elderly people. Particularly, gonarthrosis causes pain in the knee joint and reduction in the movement range, and in some cases, people cannot walk in a case where the symptoms progress. It is necessary to calculate the quantitative value of cartilage of the joint, that is, to quantify cartilage, in order to diagnose such osteoarthrosis. For this reason, various methods for quantifying cartilage of the joint using a three-dimensional image have been proposed. For example, a method for calculating the area or the volume of cartilage in the knee joint from image data of the three-dimensional image, as quantification parameters indicating the condition of a disease is proposed in JP2009-512524A. In addition, a configuration for generating a thickness map representing the thickness of cartilage in the knee joint is also disclosed in JP2009-512524A. In addition, a method for generating three-dimensional images of a bone region and a cartilage region regarding the knee joint is proposed in JP2013-48788A.

SUMMARY

However, in a case of quantifying cartilage using three-dimensional images, the accuracy of the quantification depends on the extraction results of cartilage. Here, cartilage exists over a wide range on the surface of the joint having a three-dimensional structure. There is a portion which rubs with the joint and a portion which does not rub with the joint. For this reason, in a case where the entire region of cartilage in the joint is extracted as disclosed in JP2009-512524A and JP2013-48788A described above, even in a case where cartilage is quantified, the calculated quantitative value may vary depending on which portion of the cartilage in the joint is to be evaluated for the quantification. For this reason, it can be considered that a region to be evaluated for the quantification of cartilage is set, on a three-dimensional image. However, since the joint has a three-dimensional structure, it is extremely difficult to determine the evaluation range of a region of cartilage existing in the joint.

The present invention has been made in consideration of the above-described circumstances, and an object of the present invention is to appropriately determine a region to be evaluated for quantification in a case where cartilage is quantified by calculating a quantitative value of cartilage in the joint using a three-dimensional image.

A cartilage quantification device according to the present invention comprises: region extraction unit for extracting a cartilage region within a joint of a subject from a three-dimensional image indicating the joint; projection direction determination unit for determining a projection direction of the cartilage region; projection image generation unit for generating a projection image by projecting the cartilage region in the determined projection direction; and quantification unit for calculating a quantitative value of the cartilage region on the projection image.

In the cartilage quantification device according to the present invention, the region extraction unit may extract a bone region from the three-dimensional image, and the projection image generation unit may generate the projection image by projecting the bone region and the cartilage region in the determined projection direction.

In addition, in the cartilage quantification device according to the present invention, the quantification unit may calculate the quantitative value in a subchondral bone region on the projection image.

In addition, in the cartilage quantification device according to the present invention, the quantification unit may calculate a ratio of the area of the cartilage region within the subchondral bone region to the area of the subchondral bone region, as the quantitative value.

In addition, in the cartilage quantification device according to the present invention, the quantification unit may calculate a deficiency area of the cartilage region in the subchondral bone region as the quantitative value.

In addition, in the cartilage quantification device according to the present invention, the quantification unit may calculate a representative value of a thickness of the cartilage region at each position within the subchondral bone region as the quantitative value.

The "representative value" may be any value as long as the value represents the thickness of the cartilage region at each position within the subchondral bone region. For example, it is possible to use an average value, an intermediate value, a minimum value, a maximum value, or the like of the thickness as the representative value.

In addition, in the cartilage quantification device according to the present invention, the quantification unit may calculate a thickness of the cartilage region at each position within the subchondral bone region as the quantitative value.

In addition, in the cartilage quantification device according to the present invention, the quantification unit may generate a thickness map of the cartilage region in the subchondral bone region.

In addition, in the cartilage quantification device according to the present invention, the quantification unit may calculate the quantitative value in only a region in which the thickness of the cartilage region in the subchondral bone region is greater than or equal to a predetermined threshold value.

In addition, in the cartilage quantification device according to the present invention, the quantification unit may calculate the quantitative value in a region designated in the subchondral bone region on the projection image.

In addition, in the cartilage quantification device according to the present invention, the quantification unit may divide the subchondral bone region on the projection image and calculate the quantitative value in each of the regions obtained through the division.

In addition, in the cartilage quantification device according to the present invention, the quantification unit may extract the subchondral bone region from the bone region or the cartilage region on the projection image.

In addition, in the cartilage quantification device according to the present invention, the quantification unit may extract a region, in which a region within a predetermined range is excluded from an edge of the cartilage region on the projection image, as the subchondral bone region.

In addition, in the cartilage quantification device according to the present invention, in a case where there is a calculation result of a previous quantitative value for the same subject as the subject, the quantification unit may extract a subchondral bone region at the same position as that in a case where the previous quantitative value has been calculated.

In addition, in the cartilage quantification device according to the present invention, the quantification unit may calculate an area of the cartilage region on the projection image as the quantitative value.

In addition, in the cartilage quantification device according to the present invention, the quantification unit may calculate a volume of the cartilage region on the projection image as the quantitative value.

In addition, in the cartilage quantification device according to the present invention, the joint may be a knee joint, an elbow joint, a hip joint, a shoulder joint, or an intervertebral joint.

In addition, in the cartilage quantification device according to the present invention, the projection direction determination unit may determine a body axis direction of the subject or a direction determined by using anatomical features of the subject, as the projection direction.

In addition, in the cartilage quantification device according to the present invention, the projection image generation unit may generate the projection image through parallel projection.

In addition, in the cartilage quantification device according to the present invention, the projection image generation unit may generate the projection image through point projection.

In addition, in the cartilage quantification device according to the present invention, in a case where there is a calculation result of a previous quantitative value for the same subject as the subject, the projection image generation unit may generate the projection image through projecting the cartilage region in the same projection direction as that in a case where the previous quantitative value has been calculated.

A cartilage quantification method according to the present invention comprises: extracting a cartilage region within a joint of a subject from a three-dimensional image indicating the joint; determining a projection direction of the cartilage region; generating a projection image by projecting the cartilage region in the determined projection direction; and calculating a quantitative value of the cartilage region on the projection image.

The cartilage quantification method of a joint according to the present invention may be provided as a program for causing a computer to execute the cartilage quantification method.

According to the present invention, a projection direction of an extracted cartilage region is determined, a projection image is generated by projecting the cartilage region in the determined projection direction, and a quantitative value of the cartilage region on the projection image is calculated. It is possible to appropriately determine a region for quantifying the cartilage region using the projection image in this manner. Accordingly, it is possible to obtain a stable diagnostic result of the cartilage using the calculated quantitative value.

BRIEF DESCRIPTION OF THE DRAWINGS

FIG. 11 is a view for illustrating calculation of the thickness of the cartilage region.

FIG. 12 is a view for illustrating calculation of the thickness of the cartilage region.

FIG. 13 is a view showing calculation results of quantitative values.

DETAILED DESCRIPTION

Figure 1:
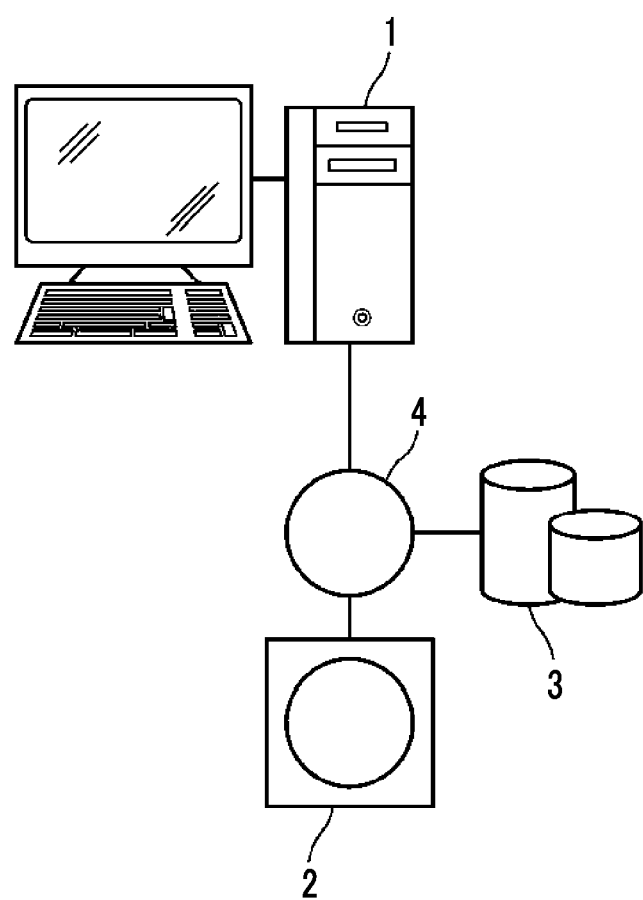
FIG. 1 is a hardware configuration diagram showing an outline of a diagnosis support system to which a cartilage quantification device according to a first embodiment of the present invention is applied.

Hereinafter, an embodiment of the present invention will be described with reference to the drawings. FIG. 1 is a hardware configuration diagram showing an outline of a diagnosis support system to which a cartilage quantification device according to an embodiment of the present invention is applied. As shown in FIG. 1, in the diagnosis support system, a cartilage quantification device 1, a three-dimensional image photographing device 2, and an image storage server 3 according to the present embodiment are connected to each other in a communicable state via a network 4. In the cartilage quantification device 1 of the diagnosis support system, a quantitative value of a cartilage region is calculated from a three-dimensional image indicating the joint of a subject.

The three-dimensional image photographing device 2 is a device generating a three-dimensional image indicating a diagnosis target site of a subject by photographing the site. Specific examples thereof include a CT device, an MRI device, and a positron emission tomography (PET) device. The three-dimensional image generated by this three-dimensional image photographing device 2 is transmitted to and stored in the image storage server 3. In the present embodiment, the diagnosis target site of a patient as a subject is a knee joint, the three-dimensional image photographing device 2 is an MRI device, and an MRI image of a knee of the subject is generated as a three-dimensional image.

The image storage server 3 is a computer that stores and manages various pieces of data, and includes a large-capacity external storage device and database management software. The image storage server 3 communicates with other devices via a wired or wireless network 4 to transmit and receive image data or the like. Specifically, various pieces of data including image data such as a three-dimensional image generated in the three-dimensional image photographing device 2 are acquired via the network and are stored in a recording medium such as a large-capacity external storage device for management. The storage format of the image data and communication between devices via the network 4 are based on the protocols of Digital Imaging and Communication in Medicine (DICOM) or the like.

The cartilage quantification device 1 is a device obtained by installing a cartilage quantification program of the present invention on a computer. The computer may be a workstation or a personal computer directly operated by a doctor who performs diagnosis or may be a server computer which is connected to the workstation or the personal computer via the network. The cartilage quantification program is recorded on and distributed in a recording medium such as a digital versatile disc (DVD) or a compact disk read only memory (CD-ROM) and is installed on a computer from the recording medium. Alternately, the cartilage quantification program is stored in a storage device of a server computer connected to a network or in a network storage in an accessible state from outside the network, and is downloaded to and installed on a computer which a doctor uses in response to a request.

Figure 2:
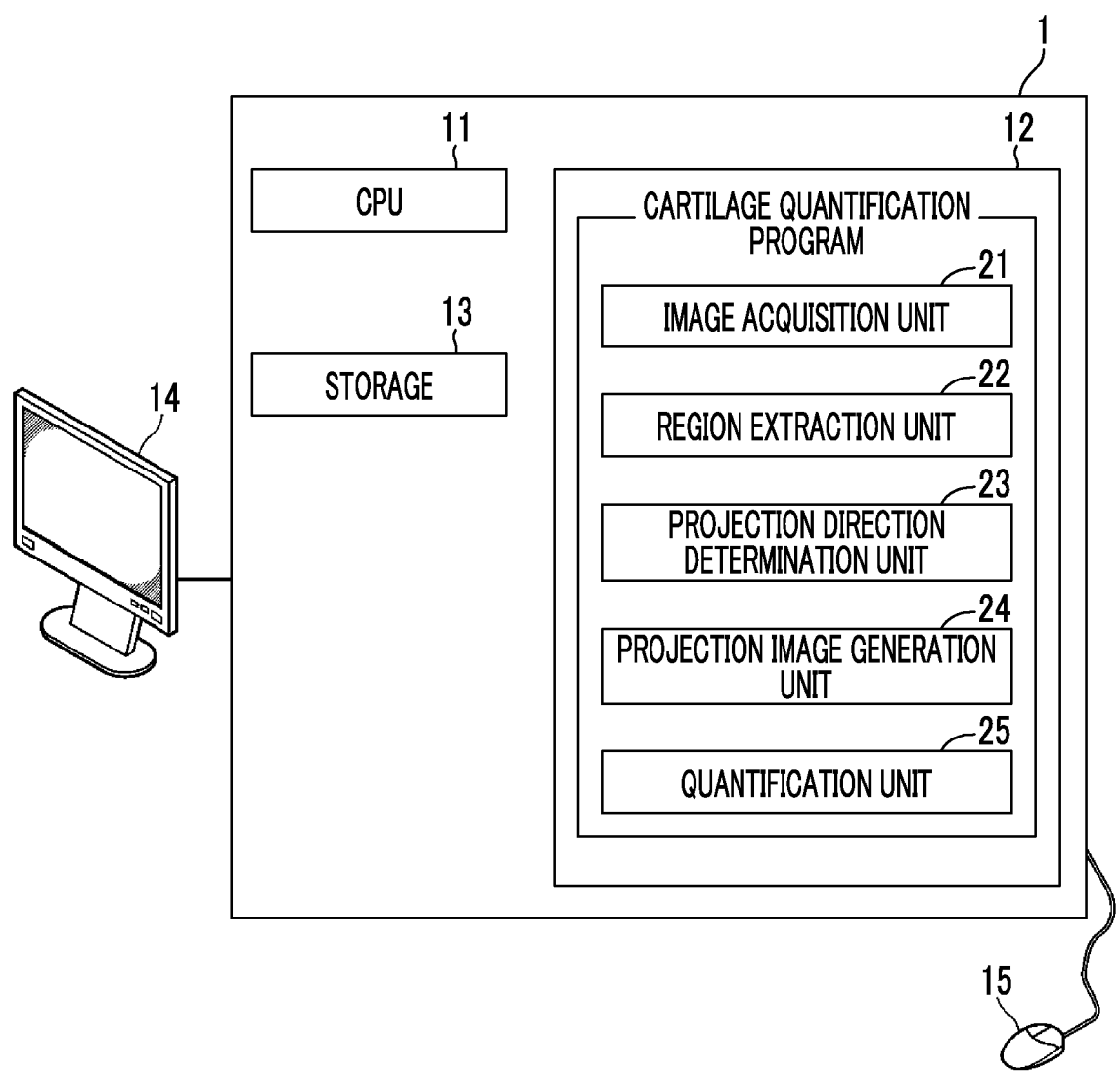
FIG. 2 is a schematic block diagram showing a configuration of the cartilage quantification device according to the first embodiment.

FIG. 2 is a view showing a schematic configuration of the cartilage quantification device realized through installing the cartilage quantification program on a computer. As shown in FIG. 2, the cartilage quantification device 1 includes a central processing unit (CPU) 11, a memory 12, and a storage 13 as a configuration of a standard workstation. In addition, a display 14 and an input unit 15 such as a mouse are connected to the cartilage quantification device 1.

Various pieces of information, which include a three-dimensional image of a subject and information necessary for a processing and are acquired from the image storage server 3 via the network 4 are stored in the storage 13. In the present embodiment, a three-dimensional image G0 in which a knee joint of a subject is set as the diagnosis target site is stored therein.

In addition, the cartilage quantification program is stored in the memory 12. The cartilage quantification program defines image acquisition processing for acquiring the three-dimensional image G0 which has been acquired by the three-dimensional image photographing device 2, region extraction processing for extracting a bone region and a cartilage region within a knee joint from the three-dimensional image G0, projection direction determination processing for determining a projection direction of the cartilage region, projection image generation processing for generating a projection image by projecting the bone region and the cartilage region in the determined projection direction, and quantification processing for calculating a quantitative value of the cartilage region on the projection image as processes executed by a CPU 11.

In a case where the CPU 11 performs those kinds of processing in accordance with the program, the computer functions as an image acquisition unit 21, a region extraction unit 22, a projection direction determination unit 23, a projection image generation unit 24, and a quantification unit 25. The cartilage quantification device 1 may include a plurality of processors or processing circuits for performing image acquisition processing, region extraction processing, projection direction determination processing, projection image generation processing, and quantification processing. The cartilage quantification device 1 of the present embodiment may be formed of only the region extraction unit 22, the projection direction determination unit 23, the projection image generation unit 24, and the quantification unit 25.

The image acquisition unit 21 acquires a three-dimensional image G0 of a knee joint of a subject from the image storage server 3. In a case where the three-dimensional image G0 is already stored in the storage 13, the image acquisition unit 21 may acquire the three-dimensional image G0 from the storage 13.

Figure 3:
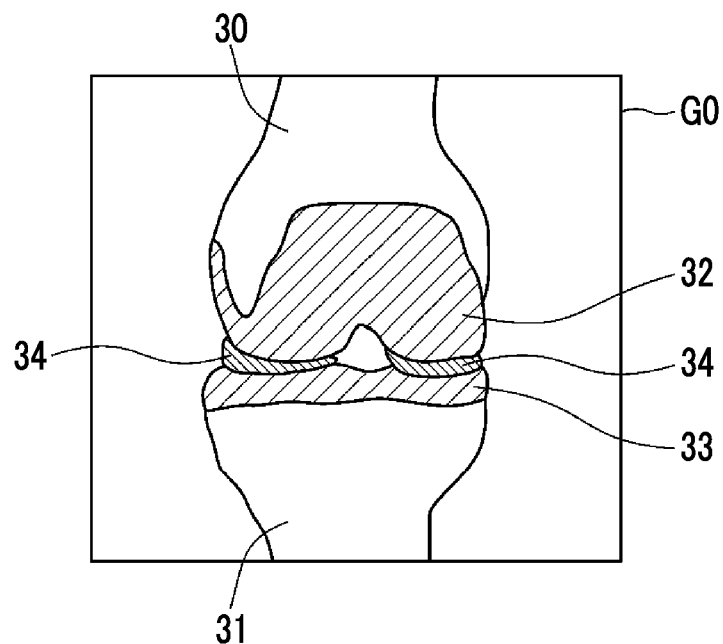
FIG. 3 is a view showing a three-dimensional image of a knee joint.

The region extraction unit 22 extracts a cartilage region within a bone region and a knee joint from the three-dimensional image G0. FIG. 3 is a view showing a three-dimensional image G0 of a knee joint. As shown in FIG. 3, a femur 30 and a tibia 31 are included in the three-dimensional image G0. In FIG. 3, the patella is omitted for explanation. There is a cartilage 32 in a portion facing the tibia 31 of the femur 30 and a cartilage 33 in a portion facing the femur 30 of the tibia 31. In addition, there is a meniscus 34 between the cartilage 32 and the cartilage 33. In the present embodiment, the three-dimensional image G0 is an MRI image. The range of pixel values (voxel values) in the three-dimensional image G0 varies in bone, cartilage, meniscus, and other regions such as muscles and fat. The region extraction unit 22 extracts a bone region and a cartilage region from the three-dimensional image G0 through threshold processing. Specifically, a region within a range which becomes a pixel value of bone is extracted as the bone region in the three-dimensional image G0. In addition, a region within a range which becomes a pixel value of cartilage is extracted as the cartilage region in the three-dimensional image G0. The femur 30 and the tibia 31 are included in the bone region and the cartilages 32 and 33 are included in the cartilage region.

In the present embodiment, the cartilages 32 and 33 that are the cartilage 32 of the femur 30 and the cartilage 33 of the tibia 31 are extracted as the cartilage regions which are then quantified as will be described below. Here, the quantification of the cartilage regions is performed through the same processing in the cartilage 32 of the femur 30 and the cartilage 33 of the tibia 31. For this reason, hereinafter, only the cartilage 32 of the femur 30 will be described as a target for quantification of a cartilage region.

Figure 4:
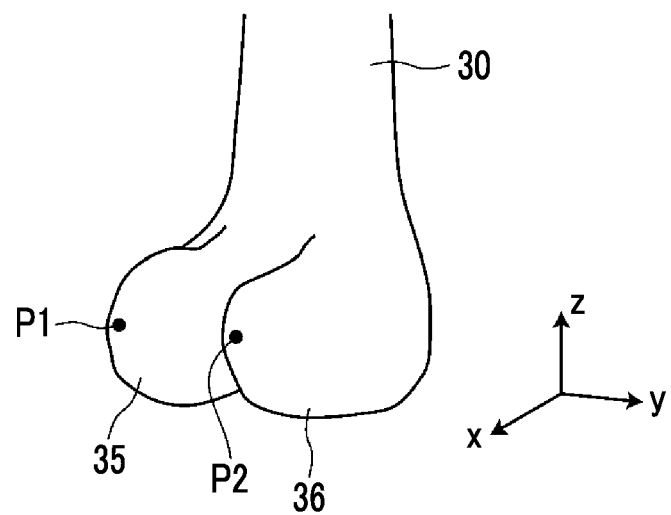
FIG. 4 is a rear-side perspective view of a femoral joint.
Figure 5:
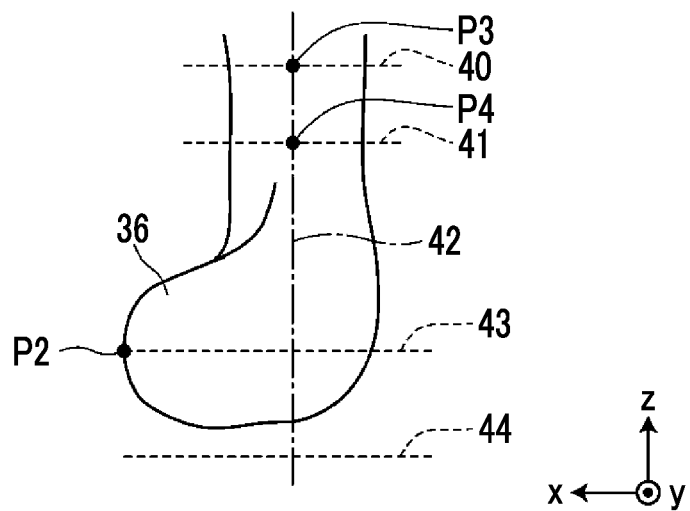
FIG. 5 is a side surface view of the femoral joint.

The projection direction determination unit 23 determines the projection direction of the cartilage region. Specifically, the projection direction is determined using anatomical features of the subject included in the three-dimensional image G0. FIG. 4 is a rear-side perspective view of a femoral joint and FIG. 5 is a side surface view of the femoral joint. FIGS. 4 and 5 show x-, y-, and z-axes set as will be described below.

Figure 6:
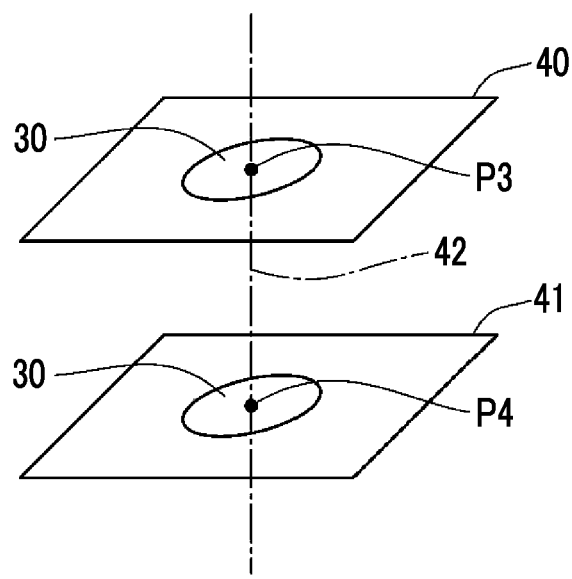
FIG. 6 is a view showing two cross sections set in the femur.

The projection direction determination unit 23 sets at least two cross sections perpendicular to an axis in the axial direction during photographing in the femur 30, that is, to a body axis. The cross sections are set at positions apart from a lower end of the femur by a predetermined distance, for example, 5 cm. This is performed in order to prevent the cross sections from being positioned at a joint portion in the femur. The space between the cross sections is also set to a predetermined distance, for example, 2 cm. FIG. 5 shows a state in which two cross sections 40 and 41 are set. FIG. 6 shows the two cross sections 40 and 41 set in the femur. The projection direction determination unit 23 calculates centers of gravity P3 and P4 of the region of the femur 30 in each of the cross sections 40 and 41. A straight line connecting the center of gravity P3 to the center of gravity P4 is set as a femoral central line 42, and a direction in which the femoral central line 42 extends toward the tibia 31 is determined as the projection direction. In addition, an axis extending in a direction opposite to the projection direction is set as a z-axis.

On the other hand, there is a medial condyle 35 and a lateral condyle 36 in the joint of the femur 30 as shown in FIG. 4. The projection direction determination unit 23 extracts points, which are respectively positioned at the medial condyle 35 and the lateral condyle 36 and are farthest from the femoral central line 42, as characteristic points P1 and P2. Since only the lateral condyle 36 appears in FIG. 5, only the characteristic point P2 is shown in FIG. 5. The projection direction determination unit 23 sets an axis directed toward the right direction in FIG. 4 while passing through the characteristic points P1 and P2, as a y-axis. Furthermore, the projection direction determination unit 23 sets an axis orthogonal to the y-axis and the z-axis is set as an x-axis. Furthermore, the projection direction determination unit 23 sets a plane 43 which is orthogonal to the femoral central line 42 and passes through the characteristic points P1 and P2 as shown in FIG. 5. The projection direction determination unit sets a projection surface 44 by shifting the plane 43 in parallel to a position away from a lower end of the femur by a predetermined distance.

The body axis direction may be simply determined as the projection direction instead of setting the direction of the femoral central line 42 as the projection direction.

Figure 7:
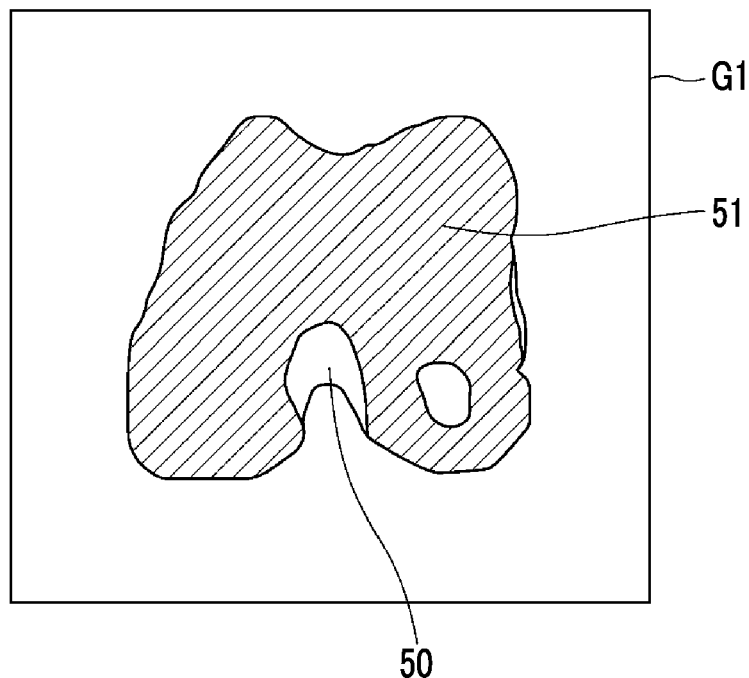
FIG. 7 is a view showing a projection image.

The projection image generation unit 24 generates a projection image G1 by projecting a bone region and a cartilage region on the projection surface 44 in the determined projection direction. Specifically, different colors are respectively allocated to the bone region and the cartilage region through a volume rendering method and the bone region and the cartilage region are projected on the projection surface 44 shown in FIG. 5. FIG. 7 is a view showing a projection image. The projection image G1 includes a bone region 50 and a cartilage region 51 in the femoral joint as shown in FIG. 7. Hatched lines are provided in the cartilage region 51 in FIG. 7. The projection image G1 may be generated through parallel projection with respect to the determined projection direction or may be generated through point projection from a point on the femoral central line 42. In the present embodiment, the projection image G1 is set to be generated through parallel projection.

Figure 8:
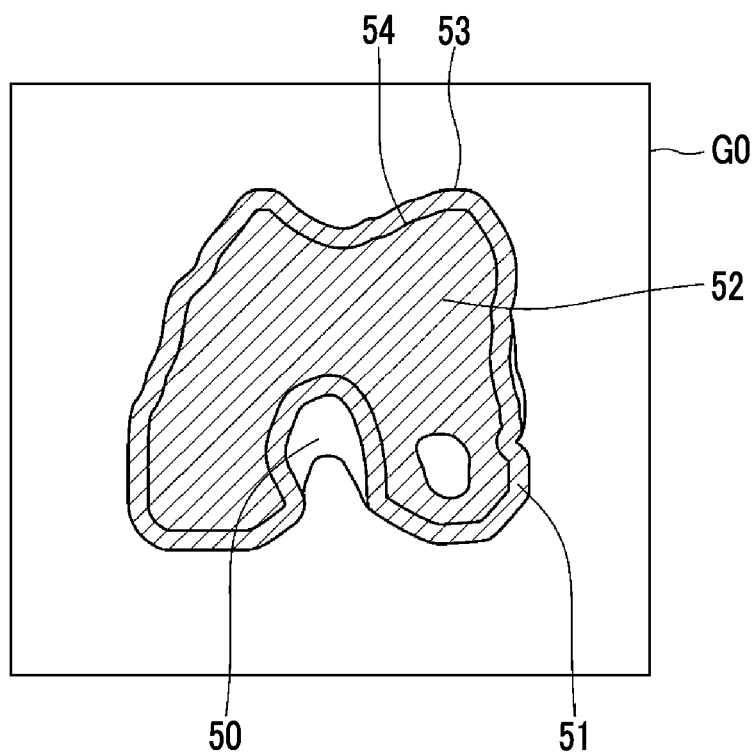
FIG. 8 is a view for illustrating extraction of a subchondral bone region.

The quantification unit 25 calculates a quantitative value of the cartilage region 51 on the projection image G1. Specifically, the quantitative value in a subchondral bone region on the projection image G1 is calculated. The subchondral bone region is a region rubbing against the joint of the tibia in the femoral joint. The peripheral portion of the cartilage region 51 in the projection image G1 does not rub against the joint of the tibia. For this reason, the quantification unit 25 extracts a region, in which a region within a predetermined range is excluded from an edge of the cartilage region 51 of the projection image G1, as the subchondral bone region. FIG. 8 is a view for illustrating the extraction of the subchondral bone region. As shown in FIG. 8, the quantification unit 25 sets a boundary line 54 at a predetermined position from an edge 53 of the cartilage region 51 in the projection image G1. The quantification unit extracts a region surrounded by the boundary line 54 as a subchondral bone region 52.

Figure 9:
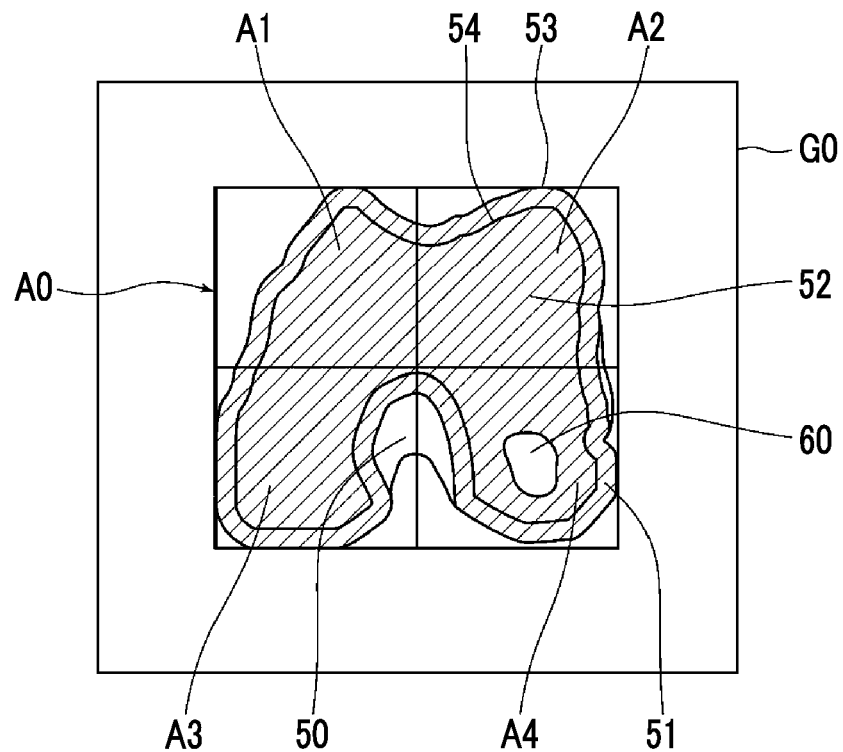
FIG. 9 is a view for illustrating division of the subchondral bone region.

Furthermore, the quantification unit 25 divides the extracted subchondral bone region 52. For example, as shown in FIG. 9, the quantification unit 25 sets a rectangular region A0 including the cartilage region 51 and divides the subchondral bone region 52 into four regions A1 to A4 by equally dividing the rectangular region A0 into four sections. The rectangular region A0 may set so as to include only the subchondral bone region 52. In addition, the number of regions divided is not limited to four, and may be two, six, or more. In addition, the regions A1 to A4 are respectively positioned on a front right side, a front left side, a rear right side, and a rear left side in the femoral joint.

Next, the quantification unit 25 calculates the area or the subchondral bone region 52 and the area of the cartilage region 51 in the subchondral bone region 52 for each of the regions A1 to A4. The area per pixel is known in the projection image G1. For this reason, the quantification unit 25 counts the number of pixels of the subchondral bone region 52 and the cartilage region 51 in each of the regions A1 to A4 and the area per pixel is multiplied by the counted number of pixels to calculate the area of the cartilage region 51 and the area of the subchondral bone region 52. The area of the cartilage region 51 is one of the quantitative values.

Figure 10:
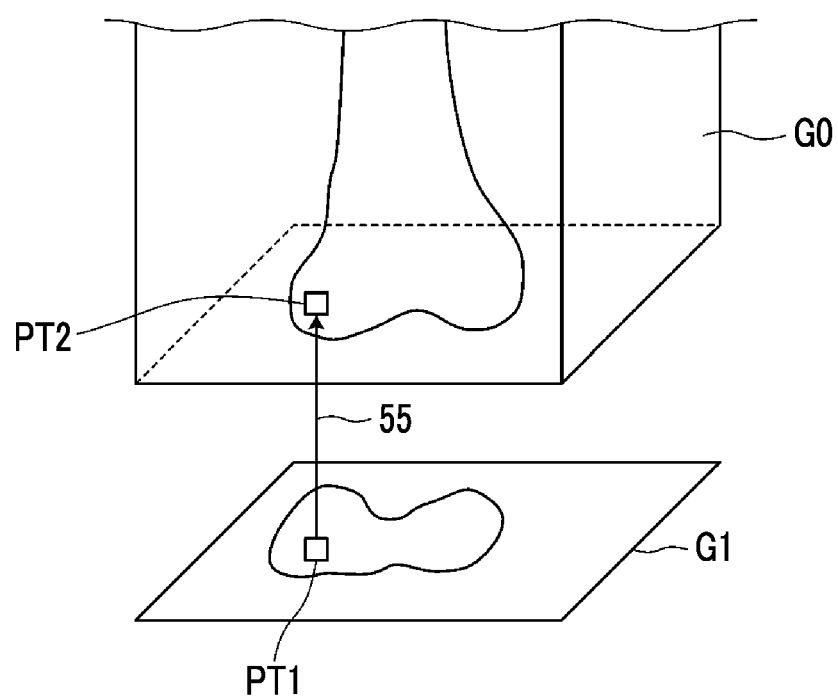
FIG. 10 is a view for illustrating calculation of the thickness of a cartilage region.

The quantification unit 25 calculates the thickness of the cartilage region 51 in each of the regions A1 to A4. FIGS. 10 to 12 are views for illustrating the calculation of the thickness of the cartilage region 51. As shown in FIG. 10, the quantification unit 25 inversely projects a pixel position PT1 at which the thickness of the cartilage region 51 of the projection image G1 is to be measured (hereinafter, referred to as a target pixel position) on the three-dimensional image G0. The direction of the inverse projection becomes a direction opposite to the projection direction determined by the projection direction determination unit 23, that is, a z-axis direction. A projection line 55 indicating the projection direction is shown in FIG. 10. In addition, the pixel position of the cartilage region of the three-dimensional image G0 corresponding to the target pixel position PT1 is set as a corresponding pixel position PT2.

The quantification unit 25 counts the number of pixels from the corresponding pixel position PT2 to the surface of the bone region 50 in the projection line 55 as shown in FIG. 11. Here, since the volume per pixel is known in the three-dimensional image G0, the length per pixel in the direction along the projection line 55 can also be known. The quantification unit 25 calculates the thickness of the cartilage region 51 in the corresponding pixel position PT2 by multiplying the length per pixel by the counted number of pixels. The thickness of the cartilage region 51 is one of the quantitative values. The quantification unit 25 calculates the thickness of the cartilage region 51 at all pixel positions in each of the regions A1 to A4. The number of voxels of the cartilage region 51 is counted by calculating the thickness of the cartilage region 51 at all the pixel positions in each of the regions A1 to A4. For this reason, it is possible to calculate the volume of the cartilage region 51 in each of the regions A1 to A4 by calculating the thickness of the cartilage region 51 at all the pixel positions in each of the regions A1 to A4.

In addition, as shown in FIG. 12, the thickness of the cartilage region 51 at the target pixel position PT1 may be calculated by calculating a pixel position PT3 of the surface of the bone region 50 and a normal line 56 at the pixel position PT3 on the projection line 55, obtaining the number of pixels from the pixel position PT3 to a pixel position PT4 of the surface of the cartilage region 51 on the normal line 56, and multiplying the length per pixel by the obtained number of pixels.

The quantification unit 25 calculates other quantitative values from the thickness and the area of the cartilage region 51 in each of the regions A1 to A4. Specifically, the ratio of the area of the cartilage region 51 within the subchondral bone region 52 to the area of the subchondral bone region 52, a deficiency area of the cartilage region 51 in the subchondral bone region 52, and a representative value of the thickness of the cartilage region 51 at each position within the subchondral bone region 52 are calculated as the quantitative values. The calculation results of the quantitative values are shown in FIG. 13. In FIG. 13, the representative value of the thickness of the cartilage region 51 is represented as a "cartilage thickness".

The ratio of the area of the cartilage region 51 within the subchondral bone region 52 to the area of the subchondral bone region 52 is obtained by calculating (the area of the cartilage region 51 within the subchondral bone region 52)/(the area of the subchondral bone region 52) for each of the regions A1 to A4.

The deficiency area of the cartilage region 51 in the subchondral bone region 52 is obtained by calculating the area of a portion in which there is no cartilage region 51 in the subchondral bone region 52 for each of the regions A1 to A4. For example, a region 60 in the region A4 shown in FIG. 9 is a deficiency region with deficient cartilage. Therefore, the area of the region 60 becomes a deficiency area of the cartilage region 51.

The representative value of the thickness of the cartilage region 51 at each position within the subchondral bone region 52 is obtained, for example, by calculating an average value, an intermediate value, a minimum value, or a maximum value of the thickness of the cartilage region 51 in the subchondral bone region 52 as the representative value. In FIG. 13, average values are shown as representative values of the thickness thereof.

Figure 14:
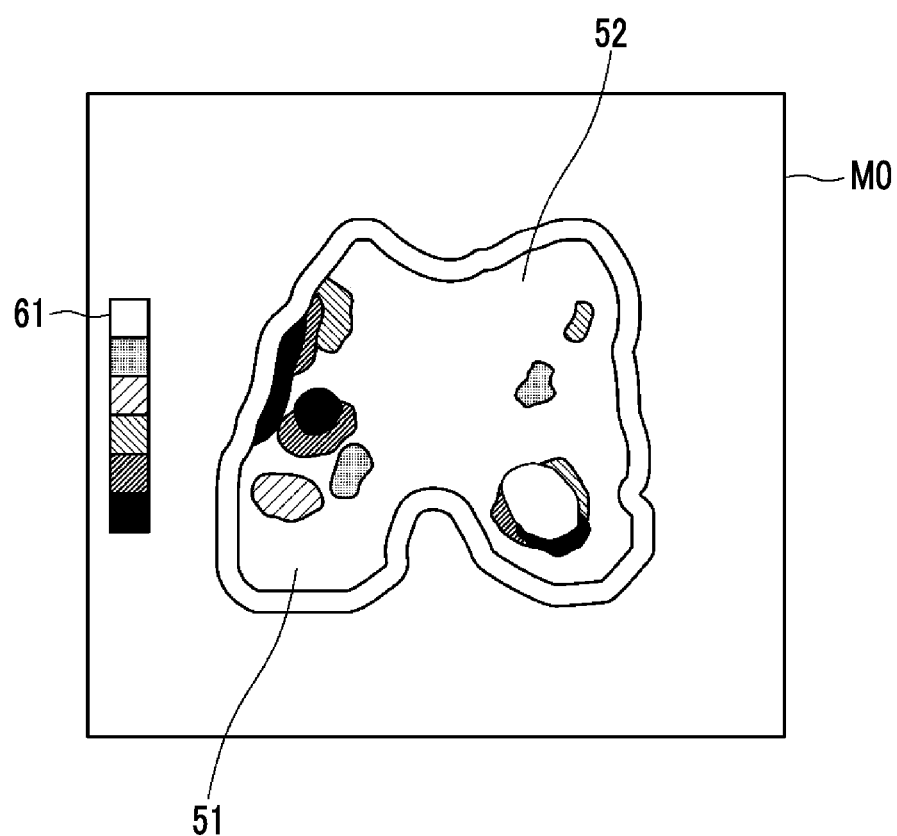
FIG. 14 is a view showing a thickness map.

In addition, the quantification unit 25 generates a thickness map from the thickness of the cartilage region 51 at each position within the subchondral bone region 52. FIG. 14 is a view showing a thickness map. In a thickness map M0, distribution of the thickness of the cartilage region 51 in the subchondral bone region 52 is shown using 6 stages of color as shown in FIG. 14. In the thickness map M0, the darker the color is, the thinner the cartilage region 51 is. In FIG. 14, different colors are indicated by different kinds of hatching. In addition, a reference 61 showing a relationship between the color and the thickness is included in the map M0. It is possible to easily recognize visually the distribution of the thickness of the cartilage region 51 in the subchondral bone region 52 by referring to the reference 61.

The quantification unit 25 may calculate a quantitative value using only a pixel position at which the thickness of the cartilage region 51 becomes greater than or equal to a threshold value. For example, the quantitative value may be calculated using only a pixel position at which the thickness of the cartilage region 51 is greater than or equal to 0.5 mm. In this case, the quantitative value is not calculated at a pixel position at which the thickness of cartilage is less than 0.5 mm. Accordingly, it is possible to exclude a region of which the thickness is thin and which does not function as cartilage from the calculation of the quantitative value. In a case where the deficiency area is set as a quantitative value, the deficiency area may be calculated by setting the pixel position, at which the thickness of cartilage is less than 0.5 mm, as a pixel position with deficient cartilage.

The calculated quantitative value is transmitted to and stored in the image storage server 3 together with information such as the name of a patient, photographing date and time, the projection direction, the position of the subchondral bone region 52, and the projection image G1, by corresponding to the three-dimensional image G0.

Figure 15:
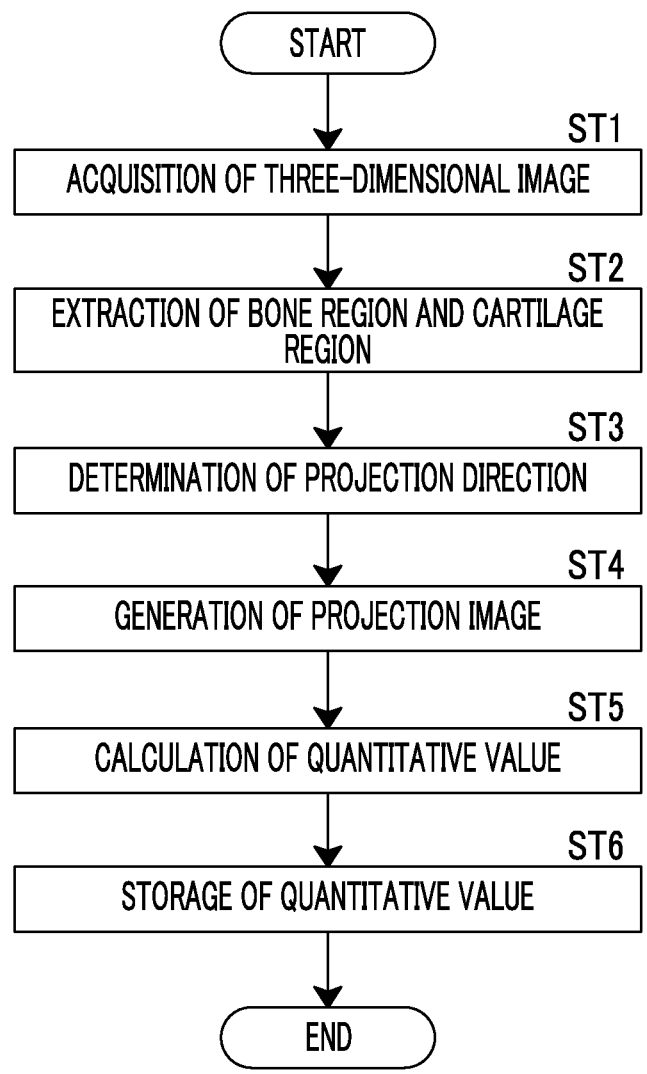
FIG. 15 is a flowchart showing processing performed in the first embodiment.

Next, processing performed in the present embodiment will be described. FIG. 15 is a flowchart showing processing performed in a first embodiment. First, the image acquisition unit 21 acquires the three-dimensional image G0 (Step ST1), and the region extraction unit 22 extracts the bone region 50 and the cartilage region 51 from the three-dimensional image G0 (Step ST2). Next, the projection direction determination unit 23 determines the projection direction of the cartilage region 51 (Step ST3), and the projection image generation unit 24 generates the projection image G1 by projecting the bone region 50 and the cartilage region 51 in the determined projection direction (Step ST4). Then, the quantification unit 25 calculates the quantitative value of the cartilage region 51 on the projection image G1 (Step ST5), the calculated quantitative value is stored in the image storage server 3 (Step ST6), and processing is completed.

In this manner, in the present embodiment, the projection direction of the extracted cartilage region 51 is determined, the projection image G1 is generated by projecting the cartilage region 51 in the determined projection direction, and the quantitative value of the cartilage region 51 on the projection image G1 is calculated. It is possible to appropriately determine a region for quantifying the cartilage region 51 using the projection image G1 in this manner. Accordingly, it is possible to obtain a stable diagnosis result of cartilage using the calculated quantitative value.

Next, a second embodiment of the present invention will be described. The configuration of a cartilage quantification device according to the second embodiment is the same as that of the cartilage quantification device according to the first embodiment shown in FIG. 2, and only processing of the second embodiment which is to be performed is different from that of the first embodiment. Therefore, the detailed description of the device will not be repeated herein. The second embodiment is different from the first embodiment from the viewpoint of performing processing for comparing a quantitative value which has been acquired in the past and calculated from the three-dimensional image G0 with a quantitative value calculated from a new three-dimensional image G0, regarding the same subject.

Figure 16:
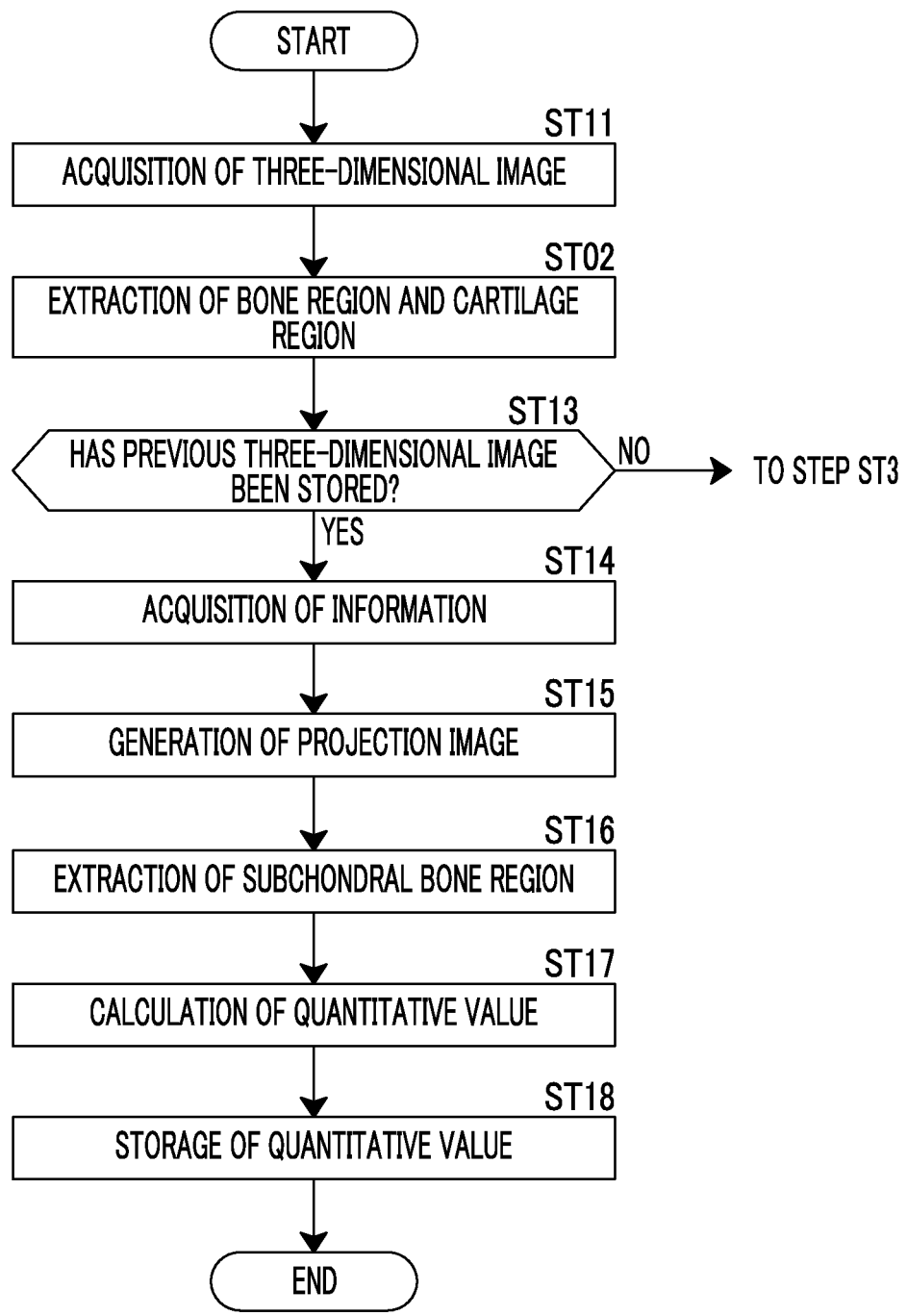
FIG. 16 is a flowchart showing processing performed in a second embodiment.

FIG. 16 is a flowchart showing the processing performed in the second embodiment. First, the image acquisition unit 21 acquires the three-dimensional image G0 (Step ST11), and the region extraction unit 22 extracts the bone region 50 and the cartilage region 51 from the three-dimensional image G0 (Step ST12). Next, the projection direction determination unit 23 determines whether a three-dimensional image G0 to be processed is stored in the image storage server 3 using the previous three-dimensional image G0 of the same subject corresponding to the quantitative value (Step ST13). In a case where Step ST13 is positive, the projection direction determination unit 23 acquires the information of the projection direction and the information of the position of the subchondral bone region 52 which have been stored in association to the previous three-dimensional image G0 of the same subject, from the image storage server 3 (Information acquisition: Step ST14).

Next, the projection image generation unit 24 generates the projection image G1 by projecting the bone region 50 and the cartilage region 51 in the same projection direction as that in a case where the previous quantitative value has been calculated, based on the acquired information (Step ST15). The quantification unit 25 extracts the subchondral bone region 52 at the same position as that in a case where the previous quantitative value has been calculated, from the projection image G1 based on the acquired information (Step ST16), calculates the quantitative value of the cartilage region 51 on the projection image G1 (Step ST17), and stores the calculated quantitative value in the image storage server 3 (Step ST18), and the processing is completed.

In contrast, in a case where Step ST13 is negative, the process proceeds to Step ST3 of the above-described first embodiment, the determination of the projection direction, the generation of the projection image, the calculation of the quantitative value, and the storage of the quantitative value are performed in the same manner as in the above-described first embodiment, and the processing is completed.

In this manner, in the second embodiment, in a case where there is a calculation result from the previous quantitative value regarding the same subject, the projection image G1 is generated by projecting a cartilage region in the same projection direction as in a case where the previous quantitative value has been calculated. For this reason, it is possible to accurately compare the quantitative value of the previous cartilage with the quantitative value of the new cartilage.

In addition, in a case where there is a calculation result of the previous quantitative value regarding the same subject, the same subchondral bone region 52 as that in a case where the previous quantitative value has been calculated is extracted from the bone region 50 on the projection image G1. Therefore, it is possible to accurately compare the quantitative value of the previous cartilage with the quantitative value of the new cartilage.

Figure 17:
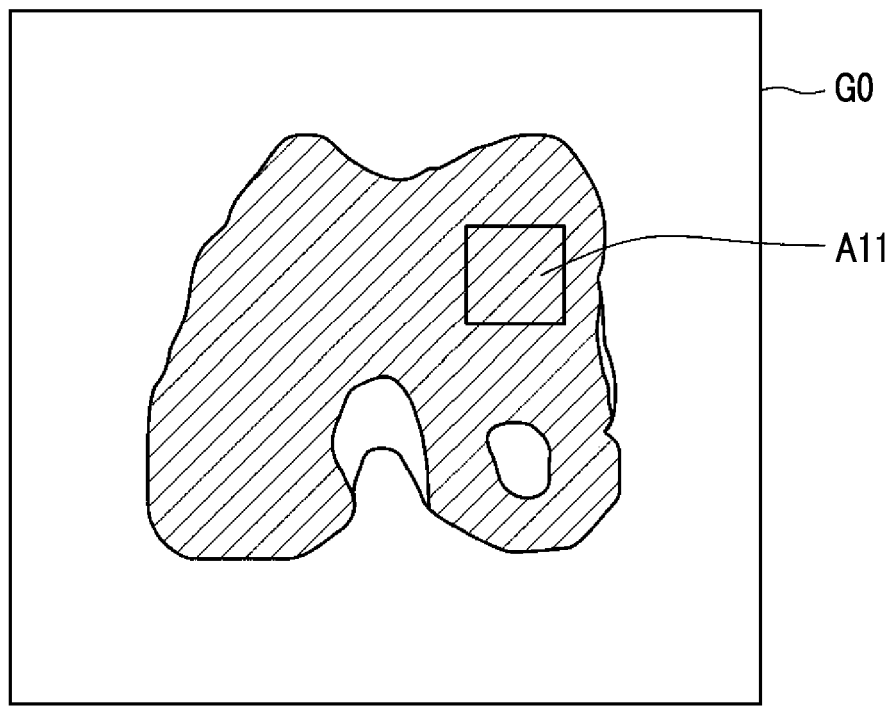
FIG. 17 is a view for illustrating manual setting of a region.

In each of the above-described embodiments, the subchondral bone region 52 is divided into the four regions A1 to A4 and the quantitative value is calculated for each of the regions A1 to A4. However, the quantitative value may be calculated over the entire subchondral bone region 52 without dividing the region. In addition, the projection image G1 may be displayed on the display 14 and an operator may designate a region for calculating the quantitative value. For example, in the projection image G1 displayed on the display 14, a region A1 may be set in the cartilage region 51 as shown in FIG. 17 using the input unit 15. In this case, the quantification unit 25 calculates quantitative value in the set region A1. A plurality of regions A1 may be set.

In addition, in each of the above-described embodiments, the subchondral bone region 52 is extracted from the bone region 50 and the quantitative value in the subchondral bone region 52 is calculated. However, the quantitative value may be calculated over the entire bone region 50 included in the projection image G1 without extracting the subchondral bone region 52. In addition, the quantitative value may be calculated from only the cartilage region 51 included in the projection image G1. In this case, the area proportion is set not to be included as the quantitative value.

In addition, in each of the above-described embodiments, representative values of the area of the subchondral bone region 52, the area of the cartilage region 51 in the subchondral bone region 52, the thickness of the cartilage region 51, the volume of the cartilage region 51, the ratio of the area of the cartilage region 51 within the subchondral bone region 52 to the area of the subchondral bone region 52, the deficiency area of the cartilage region 51 in the subchondral bone region 52, and the thickness of the cartilage region 51 at each position within the subchondral bone region 52 are calculated as the quantitative values. However, any one of these quantitative values or an arbitrary combination thereof may be calculated.

In addition, in the above-described embodiments, the quantitative values of cartilage of the knee joint are calculated. However, the present invention is not limited thereto. As a matter of course, it is possible to provide the present invention in a case of calculating the quantitative values of cartilage of the elbow joint, the hip joint, the shoulder joint, or the intervertebral joint.

In addition, in each of the above-described embodiments, the region extraction unit 22 extracts the bone region 50 and the cartilage region 51. However, only the cartilage region 51 may be extracted. In this case, only the cartilage region 51 is included in the projection image G1.

Hereinafter, the effect of the present embodiment will be described.

By extracting the bone region from the three-dimensional image and generating the projection image through projecting the bone region and the cartilage region, it is possible to calculate the quantitative values of the cartilage region while comparing the quantitative values of the cartilage region with those of the bone region.

By calculating the quantitative values in the subchondral bone region on the projection image, it is possible to calculate the quantitative values of the cartilage region while more appropriately comparing the quantitative values of the cartilage region with those of the bone region.

By calculating the quantitative values in only a region in which the thickness of the cartilage region in the subchondral bone region becomes greater than or equal to a predetermined threshold value, it is possible to exclude a region of which the thickness is thin and which does not function as cartilage from the calculation of the quantitative values. Therefore, it is possible to perform more appropriate diagnosis on the cartilage.

By calculating the quantitative values in a region designated in the subchondral bone region on the projection image, it is possible to obtain a stable diagnosis result of the cartilage in the designated region.

By extracting a region, in which a region within a predetermined range is excluded from an edge of the subchondral bone region on the projection image, as the subchondral bone region, it is possible to exclude a region of the joint which does not rub against the other joint from the calculation of the quantitative values. Accordingly, it is possible to calculate the quantitative values of the actually functioning cartilage region.

By dividing the subchondral bone region on the projection image and calculating the quantitative values in each region obtained through the division, it is possible to perform appropriate diagnosis of the cartilage for each divided region.

In a case where there is a calculation result of a previous quantitative value for the same subject as the subject, it is possible to accurately compare the quantitative value of the previous cartilage with the quantitative value of the new cartilage by extracting the subchondral bone region at the same position as that in a case where the previous quantitative value has been calculated.

The joints face each other in the body axis direction of a human body. For this reason, it is possible to generate a projection image by appropriately projecting regions of the joints by determining the body axis direction of a subject as the projection direction. In addition, by appropriately determining a characteristic point in the joints, it is possible to determine the direction in which the joints face each other as the projection direction. Therefore, it is possible to generate the projection image by appropriately projecting the regions of the joints.

In a case where there is a calculation result of a previous quantitative value for the same subject as the subject, it is possible to accurately compare the quantitative value of the previous cartilage with the quantitative value of the new cartilage by generating the projection image through projecting the cartilage region in the same projection direction as that in a case where the previous quantitative value is calculated.

What is claimed is:

1. A cartilage quantification device comprising:
a processor configured to:
   extract a bone region and a cartilage region within a joint of a subject from a three-dimensional image indicating the joint;
   determine a projection direction of the cartilage region;
   generate a projection image by projecting the bone region and the cartilage region in the determined projection direction; and
   calculate a quantitative value of the cartilage region on the projection image,
wherein the processor is further configured to calculate the quantitative value in a subchondral bone region on the projection image,
wherein the processor is further configured to calculate a thickness of the cartilage region at each position within the subchondral bone region as the quantitative value,
wherein the processor is further configured to generate a thickness map of the cartilage region in the subchondral bone region, and
wherein the processor is further configured to calculate the quantitative value in only a region in which the thickness of the cartilage region in the subchondral bone region is greater than or equal to a predetermined threshold value.

2. The cartilage quantification device according to claim 1,
wherein the processor is further configured to calculate a ratio of the area of the cartilage region within the subchondral bone region to the area of the subchondral bone region, as the quantitative value.

3. The cartilage quantification device according to claim 1,
wherein the processor is further configured to calculate a deficiency area of the cartilage region in the subchondral bone region as the quantitative value.

4. The cartilage quantification device according to claim 1,
wherein the processor is further configured to calculate a representative value of a thickness of the cartilage region at each position within the subchondral bone region as the quantitative value.

5. The cartilage quantification device according to claim 1,
wherein the processor is further configured to calculate the quantitative value in a region designated in the subchondral bone region on the projection image.

6. The cartilage quantification device according to claim 1,
wherein the processor is further configured to divide the subchondral bone region on the projection image and calculates the quantitative value in each of the regions obtained through the division.

7. The cartilage quantification device according to claim 1,
wherein the processor is further configured to extract the subchondral bone region from the bone region or the cartilage region on the projection image.

8. The cartilage quantification device according to claim 7,
wherein the processor is further configured to extract a region, in which a region within a predetermined range is excluded from an edge of the cartilage region on the projection image, as the subchondral bone region.

9. The cartilage quantification device according to claim 7,
wherein, in a case where there is a calculation result of a previous quantitative value for the same subject as the subject, the processor is further configured to extract a subchondral bone region at the same position as that in a case where the previous quantitative value has been calculated.

10. The cartilage quantification device according to claim 1,
wherein the processor is further configured to calculate an area of the cartilage region on the projection image as the quantitative value.

11. The cartilage quantification device according to claim 1,
wherein the processor is further configured to calculate a volume of the cartilage region on the projection image as the quantitative value.

12. The cartilage quantification device according to claim 1,
wherein the joint is a knee joint, an elbow joint, a hip joint, a shoulder joint, or an intervertebral joint.

13. The cartilage quantification device according to claim 1,
wherein the processor is further configured to determine a body axis direction of the subject or a direction determined by using anatomical features of the subject, as the projection direction.

14. The cartilage quantification device according to claim 1,
wherein the processor is further configured to generate the projection image through parallel projection.

15. The cartilage quantification device according to claim 1,
wherein the processor is further configured to generate the projection image through point projection.

16. The cartilage quantification device according to claim 1,
wherein, in a case where there is a calculation result of a previous quantitative value for the same subject as the subject, the processor is further configured to generate the projection image through projecting the cartilage region in the same projection direction as that in a case where the previous quantitative value has been calculated.

17. A cartilage quantification method comprising:
extracting a bone region and a cartilage region within a joint of a subject from a three-dimensional image indicating the joint;
determining a projection direction of the cartilage region;
generating a projection image by projecting the bone region and the cartilage region in the determined projection direction; and
calculating a quantitative value of the cartilage region on the projection image,
wherein the quantitative value is calculated in a subchondral bone region on the projection image,
wherein a thickness of the cartilage region is calculated at each position within the subchondral bone region as the quantitative value,
wherein a thickness map of the cartilage region in the subchondral bone region is generated,
wherein the quantitative value is calculated in only a region in which the thickness of the cartilage region in the subchondral bone region is greater than or equal to a predetermined threshold value.

18. A non-transitory computer-readable recording medium having stored therein a cartilage quantification program causing a computer to execute:
a process of extracting a bone region and a cartilage region within a joint of a subject from a three-dimensional image indicating the joint;
a process of determining a projection direction of the cartilage region;
a process of generating a projection image by projecting the bone region and the cartilage region in the determined projection direction; and
a process of calculating a quantitative value of the cartilage region on the projection image,
wherein the quantitative value is calculated in a subchondral bone region on the projection image,
wherein a thickness of the cartilage region is calculated at each position within the subchondral bone region as the quantitative value,
wherein a thickness map of the cartilage region in the subchondral bone region is generated, and
wherein the quantitative value is calculated in only a region in which the thickness of the cartilage region in the subchondral bone region is greater than or equal to a predetermined threshold value.

* * * * *